(12) United States Patent
Pasricha et al.

(10) Patent No.: US 7,998,148 B2
(45) Date of Patent: *Aug. 16, 2011

(54) ENDOSCOPIC INSTRUMENTS

(75) Inventors: Pankaj Jay Pasricha, Houston, TX (US); Hideki Shimonaka, Hachioji (JP); Koichi Kawashima, Hachioji (JP); Takayuki Suzuki, Yokohama (JP); Tsuyoshi Tsukagoshi, Fuchu (JP); Yoshio Onuki, Hino (JP)

(73) Assignee: Olympus Corporation, Tokyo (JP)

( * ) Notice: Subject to any disclaimer, the term of this patent is extended or adjusted under 35 U.S.C. 154(b) by 1011 days.

This patent is subject to a terminal disclaimer.

(21) Appl. No.: 11/427,836

(22) Filed: Jun. 30, 2006

(65) Prior Publication Data
US 2006/0282100 A1    Dec. 14, 2006

Related U.S. Application Data

(62) Division of application No. 10/114,128, filed on Apr. 3, 2002, now Pat. No. 7,156,857.

(60) Provisional application No. 60/281,016, filed on Apr. 4, 2001.

(51) Int. Cl.
*A61B 17/10* (2006.01)
(52) U.S. Cl. ........................................ 606/139; 606/144
(58) Field of Classification Search .......... 606/139–150, 606/222, 223, 106, 104; 604/187–274; 600/562–584, 107, 153; 112/38, 49, 78–103, 112/220–227

See application file for complete search history.

(56) References Cited

U.S. PATENT DOCUMENTS

| | | | |
|---|---|---|---|
| 3,643,653 A | 2/1972 | Takahashi et al. | |
| 4,493,323 A | 1/1985 | Albright et al. | |
| 5,037,021 A | 8/1991 | Mills et al. | |
| 5,397,326 A | 3/1995 | Mangum | |
| 5,474,543 A | 12/1995 | McKay | |
| 5,741,277 A | 4/1998 | Gordon et al. | |
| 5,792,153 A | 8/1998 | Swain et al. | |
| 5,797,927 A * | 8/1998 | Yoon ............................. | 606/144 |
| 5,814,065 A | 9/1998 | Diaz | |
| 5,860,992 A | 1/1999 | Daniel et al. | |
| 5,887,594 A | 3/1999 | LoCicero, III | |
| 5,895,395 A * | 4/1999 | Yeung ........................... | 606/144 |
| 5,897,507 A | 4/1999 | Kortenbach et al. | |
| 5,984,932 A | 11/1999 | Yoon | |
| 5,993,466 A | 11/1999 | Yoon | |
| 6,071,233 A | 6/2000 | Ishikawa et al. | |
| 6,113,609 A | 9/2000 | Adams | |
| 6,179,776 B1 | 1/2001 | Adams et al. | |
| 6,352,503 B1 * | 3/2002 | Matsui et al. ................. | 600/104 |
| 6,409,678 B1 | 6/2002 | Ouchi | |
| 6,494,888 B1 | 12/2002 | Laufer et al. | |
| 6,551,315 B2 | 4/2003 | Kortenbach et al. | |
| 6,605,096 B1 | 8/2003 | Ritchart | |
| 6,663,639 B1 | 12/2003 | Laufer et al. | |
| 6,921,361 B2 * | 7/2005 | Suzuki et al. ................. | 600/106 |

(Continued)

FOREIGN PATENT DOCUMENTS

EP    1284120 A1    2/2003

(Continued)

*Primary Examiner* — Darwin P Erezo
*Assistant Examiner* — Christina Lauer
(74) *Attorney, Agent, or Firm* — Holtz, Holtz, Goodman & Chick, PC

(57) ABSTRACT

An endoscopic instrument used to form an artificial valve for treating gastroesophageal reflux disease (GERD).

2 Claims, 19 Drawing Sheets

U.S. PATENT DOCUMENTS

| | | | |
|---|---|---|---|
| 2002/0055757 A1* | 5/2002 | Torre et al. | 606/192 |
| 2002/0111534 A1* | 8/2002 | Suzuki et al. | 600/102 |
| 2003/0004544 A1 | 1/2003 | Kawashima | |
| 2003/0171651 A1 | 9/2003 | Page et al. | |
| 2003/0199731 A1 | 10/2003 | Silverman et al. | |
| 2003/0216753 A1 | 11/2003 | Nishtala et al. | |

FOREIGN PATENT DOCUMENTS

| | | |
|---|---|---|
| JP | 2000-033071 | 2/2000 |
| JP | 2000-037348 | 2/2000 |
| JP | 2000-157552 A | 6/2000 |
| WO | WO 99/22649 | 5/1999 |

* cited by examiner

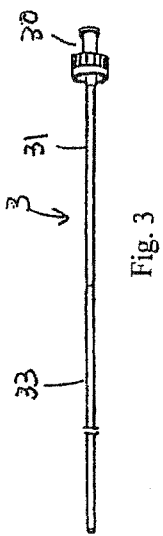
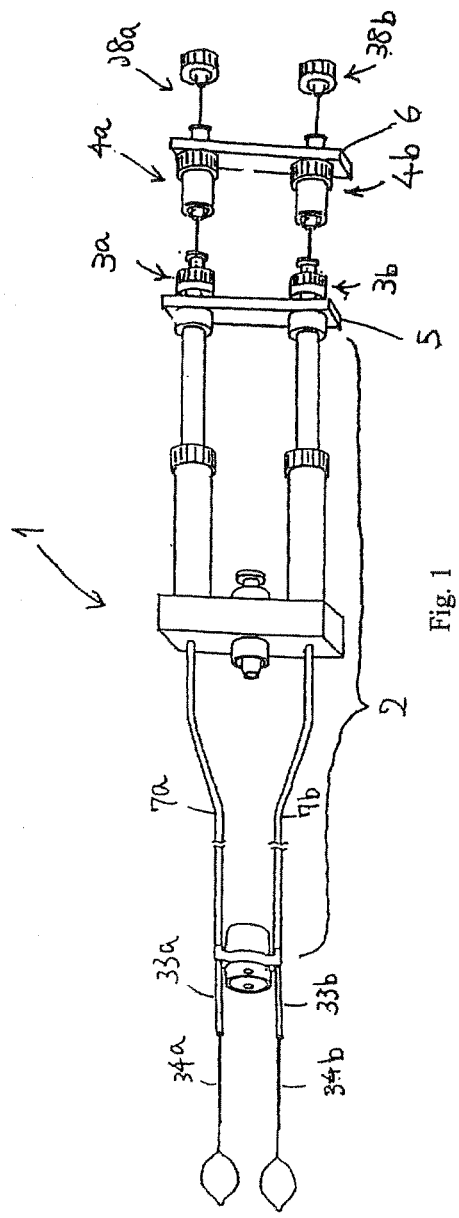
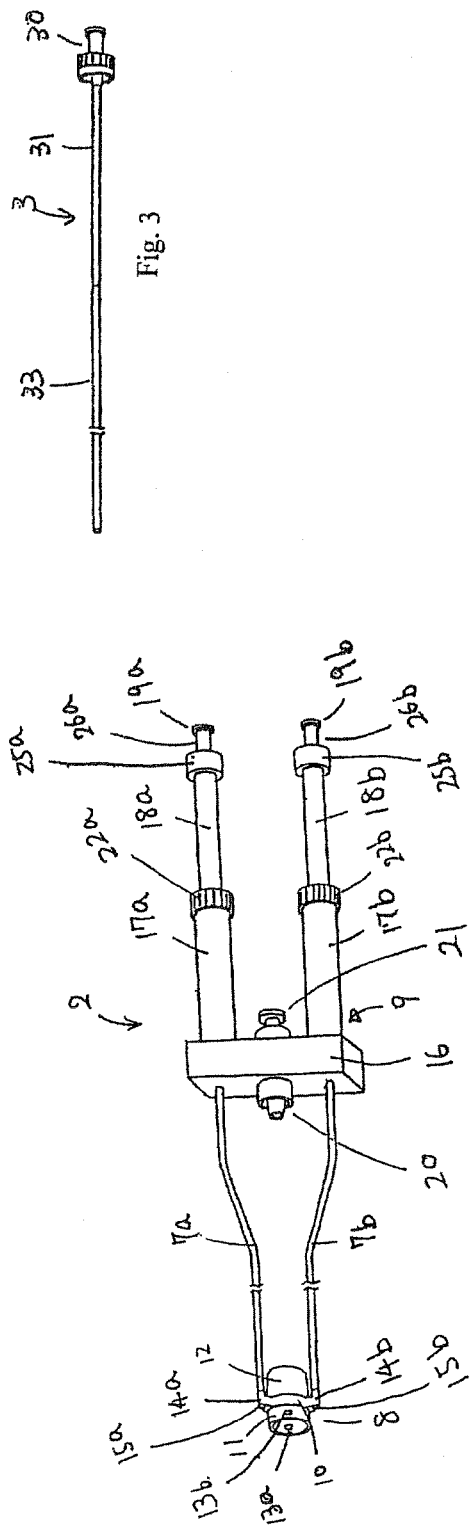

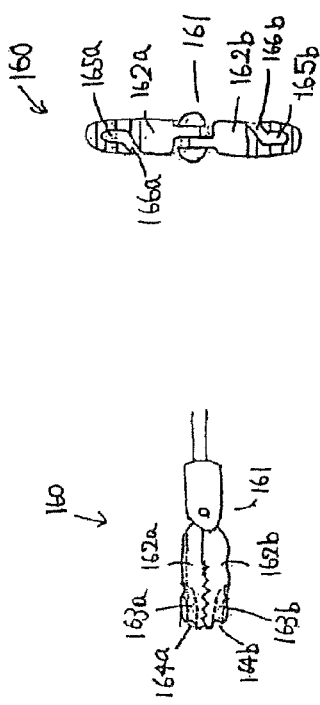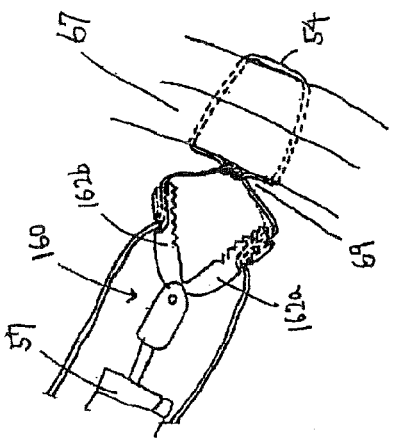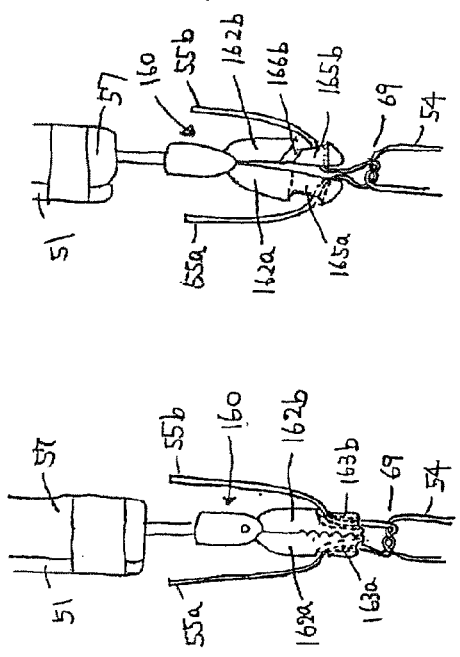
Fig. 37 (a)
Fig. 37 (b)
Fig. 38 (a)
Fig. 38 (b)
Fig. 38 (c)

ENDOSCOPIC INSTRUMENTS

CROSS-REFERENCE TO RELATED APPLICATIONS

The present application is a Divisional Application of U.S. application Ser. No. 10/114,128, filed Apr. 3, 2002 now U.S. Pat. No. 7,156,857 which claims the benefit of U.S. Provisional Application to Yoshia Onuki et al, entitled "Endoscopic Instruments," application No. 60/281,016 filed Apr. 4, 2001.

BACKGROUND OF THE INVENTION

1. Field of the Invention

The present invention relates to apparatuses for forming an artificial valve to treat gastroesophageal reflux disease (GERD).

2. Description of the Related Art

The incidence of GERD has increased recently. The main symptoms of GERD are heartburn and mucosal breaks in the esophagus. Although it is a benign disease, GERD is accompanied by serious pain, and often requires treatment. The main cause of GERD is decreased function of the lower esophageal sphincter (LES) at the bottom of the esophagus followed by reflux of acid into the esophagus. GERD is usually treated by administration of acid secretion controlling agent such as proton-pump inhibitor. Moderate GERD will improve and may be treated completely by medication. If, however, the LES function is damaged seriously or if anatomic problems such as hiatal hernias exist, treatment with medication is less effective, and becomes costly over an extended period of time.

Therefore, cases of serious GERD are often treated surgically. Effective surgical methods—including Nissen fundoplication or Toupet method—are known and applied widely. With this method, the LES is wrapped by the stomach wall to improve its function. This method has been proven highly effective. Recently, laparoscopic surgery techniques were used with this method as a less invasive treatment. Because there are many patients, and GERD is a benign disease, these less invasive treatments are most desirable.

FIG. 39 depicts a tool for transoral treatment of GERD, disclosed in U.S. Pat. No. 5,887,594. This instrument (a) comprises a piercing device (e) having an elongate portion (b), a manipulation section (c) and a hook portion (d); and a securing device (i) having a connector (f), a manipulation section (g) and a securing mechanism (h). The piercing device (e) is inserted from the mouth to the stomach of a patient, and pulled up to the esophagus (k), with the hook portion (d) fixed at the upper stomach (j) thereby forming a fold of tissue (not shown).

Then, the securing device (i) is inserted into the esophagus (k) of the patient, and the securing mechanism (h) fixes the fold consisting of the upper stomach (j) and the esophagus (k). When the fold is fixed, the intermediate portion is compressed to protrude inward to form a valve (not shown).

FIGS. 40 to 44 depict another transoral treatment method of GERD, disclosed in International Patent Publication WO99/22649. An instrument (n) has a rotatable fastener head (p), which is rotatable at the distal end of a flexible tube (o), and the rotatable fastener head (p) and/portion of the flexible tube (o) that can touch the rotatable fastener head (p) have a male fastener (q) and a female fastener (r), respectively. The flexible tube (o) has a rotatable grasper (s) at the distal end, and an opening for an endoscope (t) to be inserted throughout the flexible tube (o). First, the flexible tube (o) is inserted from the mouth to the stomach of the patient. The rotatable grasper (s) is drawn into contact with a junction (v) between the stomach and the esophagus. The rotatable grasper (s) is operated to hold the junction (v). Next, the flexible tube (o) is advanced downward to suspend the junction (v). The rotatable fastener head (p) is operated to penetrate the junction (v) with the male fastener (q) to engage with the female fastener (r). Thus, the junction (v) and the middle part are compressed to be protruded inward to form a protrusion (x).

In the composition disclosed in U.S. Pat. No. 5,887,594, the hook portion d of the piercing device (e) needs to be fixed to the stomach and pulled. The gastric wall, however, is thicker than the esophagus, and is divided into three ref ions: the inner mucous membrane; the middle proper muscularis; and the outer serous membrane. In particular, a space between the mucous membrane and the proper muscularis has high movability. To form a protrusion into a valve, tissue including the proper muscularis should be compressed and lifted up. The hook portion (d) only takes the mucous membrane and cannot include the proper muscularis below it. Thus, the valve formed in this application is not large and thick enough to prevent reflux satisfactorily.

In the apparatus disclosed in International Patent Publication WO99/22649, the rotatable grasper (s) is integral to the flexible tube (o), which makes it difficult to touch the target tissue. The field of view of the endoscope (t) is blocked by the rotatable fastener head (p), which makes difficult for the rotatable grasper (s) to hold and suspend the junction (v) between the stomach and the esophagus.

Because the position between the rotatable grasper (s), the male fastener (q) and the female fastener (r) is fixed, the size of a protrusion (x) is limited. It is desirable, however, to form a protrusion of varying size depending on the degree of severity of GERD. The difficulty of passing food has already been reported as complication of artificial cardia in Nissen fondoplication, and is likely to happen with an excessively large protrusion (x). Even much smaller protrusion (x) is effective for the treatment of the moderate GERD. With this apparatus, treatment is not flexible enough to allow a small protrusion to facilitate food flow in the case of moderate GERD. And further, the male fastener (q) is exposed outside the device, and may damage a body lumen when it is introduced into it.

SUMMARY OF THE INVENTION

The first object of the present invention is to provide the apparatus for forming a protrusion including the proper muscularis below the mucous membrane to prevent gastroesophageal reflux effectively.

The second object of the present invention is to provide the apparatus for forming a protrusion that is easy to operate and will treat in a short time.

The third object of the present invention is to provide the apparatus for holding and suspending the esophagogastric junction using a fixing device extending out of the distal end of an endoscope to improve the ease of the operation for forming the protrusion.

The fourth object of the present invention is to provide the apparatus for forming a protrusion of varying size by using a separate holding device and a piercing means to achieve the flexible treatment method, which may be modified due to the degree of GERD severity.

The fifth object of the present invention is to provide the apparatus for forming a protrusion safely without damaging a human body.

In accordance with the present invention, a tissue-piercing device, to be used with an endoscope, which has two piercing members which have a needle, also includes two slidable suture-holding means which are inserted in the each needle and are extended from or retracted into the distal ends of the needles, and at least a holding-operation means for operating the suture-holding means.

The tissue-piercing device may also include two slidable sutures which are inserted in each needle.

It may also include a slidable suture-holding means which is inserted in one needle and is extended from or retracted into the distal end of the needle, and a holding-operation means for operating the suture-holding means, and a slidable suture inserted in the other needle. It is possible for the suture-holding means to hold the suture.

The present invention is also directed to a treatment system comprising first and second endoscopes to be inserted orally into a human body; a tissue-piercing device according to the present invention being mounted to the first endoscope; a tissue-fixing device extending out of the distal end of the second endoscope and fixed at a piercing point, and a suture which is folded in a U shape and inserted into a human body using the second endoscope.

A tissue-piercing device with two slidable sutures according to the present invention may be mounted to the first endoscope; a tissue-fixing device extending out of the distal end of the second endoscope and fixed at a piercing point, and a holding means for a suture which is inserted into a human body using the second endoscope.

A tissue-piercing device with slidable suture-holding means according to the present invention may be mounted to the first endoscope; and a tissue-fixing device extending out of the distal end of the second endoscope and fixed at a piercing point.

In the tissue-piercing device according to the present invention, the two needles may be parallel and apart from each other.

There may also be operation sections at the proximal ends of the piercing members; a distal coupling member for connecting distal ends of the needles; and a proximal coupling member for connecting the operation sections of the piercing members.

The distal coupling member may be formed to be mounted to the distal end of the endoscope, and the proximal coupling member may be formed to be mounted to the operation section of the endoscope. The distal coupling member may be a cap which may be made of transparent material.

In the tissue-piercing device according each piercing member may include a flexible outer sheath, a slidable flexible inner sheath which is inserted in the outer sheath and is extended from or retracted into the distal end of the outer sheath, a slidable needle which is inserted in the inner sheath and is extended from or retracted into the distal end of the inner sheath, a housing to be connected to the proximal end of the outer sheath, an inner sheath operation means connected to the proximal end of the inner sheath for moving back and forth the inner sheath, and a needle operation means connected to the proximal end of the needle for moving back and forth the needle.

The tissue-piercing device may also include a switch means for switching between a two-piercing member operation and a separate operation.

A switch means for switching between a two-needle/inner sheath operation and a separate operation may also be provided. When the switch means selects a two-needle operation, the needle extension may be varied to allow piercing the tissue with one needle after another The suture-holding means may be loop-shaped.

A driving member for rotating or moving back and forth the suture-holding means may be provided at the proximal end of the suture-holding means, and the central axis of the suture-holding means may be inclined against the longitudinal axis of the driving member.

The tissue-piercing device, to be used with an endoscope, may include a delivery means for delivering a knot of the suture into the target site in the human body and tightening it.

The delivery means may comprise at least one hole.

The cap may have at least a side hole which performs as delivery means for delivering a knot of the suture formed outside the human body into it.

The present invention is also directed to a tissue-fixing device, to be used with an endoscope, which comprises a delivery means for delivering a knot of the suture into the target site in the human body and tightening it.

It is also directed to a knot pusher, to be used with an endoscope, comprising a pair of opening or closing jaws; and a hole made in each jaw. The jaws may also serve as a means for fixing tissue.

The endoscope may be a flexible endoscope and embodiments of the present invention may be used to suture tissue in the human body. In particular, embodiments of the present invention may be used to form an artificial valve for treating gastroesophageal reflux disease (GERD).

BRIEF DESCRIPTION OF THE DRAWINGS

FIG. 1 shows a piercing device according to a first embodiment of the present invention;

FIG. 2 shows a main body of the piercing device according to the first embodiment;

FIG. 3 shows an inner sheath according to the first embodiment;

FIGS. 37(a) and 37(b) show alternate forms of fixing-holding forceps according to a sixth embodiment of the present invention;

FIGS. 38(a) and 38(b) show sutures inserted in the fixing-holding forceps shown in FIGS. 37(a) and 37(b), respectively, and FIG. 38(c) shows the fixing-holding forceps of the sixth embodiment used to push a knot against the esophageal wall;

DESCRIPTION OF THE PREFERRED EMBODIMENTS

Figure 4:
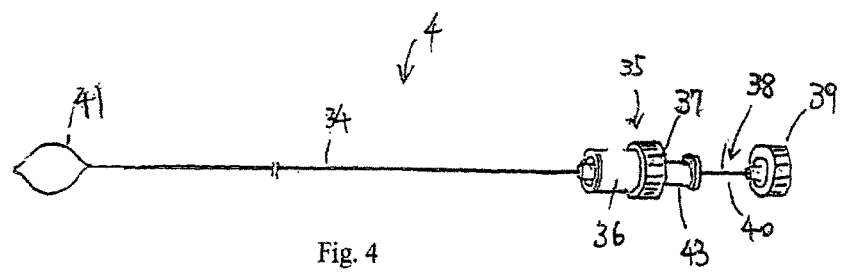
FIG. 4 shows a needle according to the first embodiment.
Figure 5:
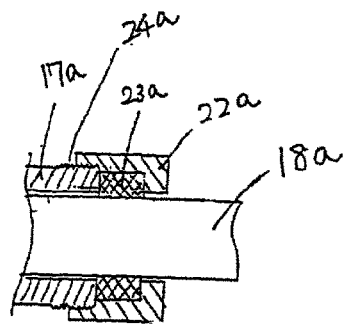
FIG. 5 is a cross-sectional view of a proximal end of a grip of the operation section of the piercing device according to the first embodiment.
Figure 6:
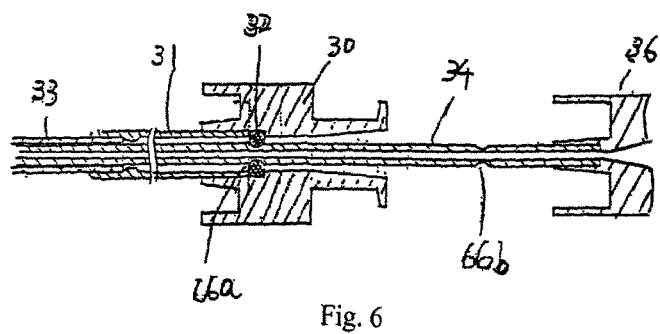
FIG. 6 is a cross-sectional view of the needle inserted into the inner sheath according to the first embodiment.
Figure 7:
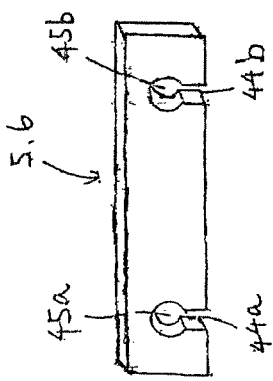
FIG. 7 shows an inner sheaths-coupling member or needles-coupling member according to the first embodiment.

First Embodiment (FIGS. 1 to 20, 29)

Description of a Piercing Device and a Knot Pusher (FIGS. 1 to 7, 10, 29)

A piercing device 1 comprises a main body 2, inner sheaths 3a and 3b, needles 4a and 4b, an inner sheaths-coupling member 5, and a needles-coupling member 6.

The main body 2 comprises two outer sheaths 7a and 7b, caps 8 connected at the distal ends of the sheaths 7a and 7b, and an operation section 9 connected at the proximal end of the sheaths 7a and 7b.

The cap 8 comprises an outer sheaths-connecting section 10, a distal cylindrical section 11, and a distal mounting section 12.

The distal cylindrical section 11 is made of a relatively hard material. Preferably, it is made of a transparent plastic material such as polycarbonate lest it should obstruct the vision of a first endoscope 27. Preferably, the inner diameter is about 5 to 15 mm, the wall thickness is about 1 mm. The length is about 3 to 10 mm, and a shorter cylinder is better. Side holes 13a and 13b are positioned at the opposite sides, apart 180 degrees each other. The side holes 13a and 13b are responsible for pushing a knot of a suture, and the piercing device 1 itself acts as a knot pusher. A suture (which will be described later) pass through the side holes 13a and 13b, which each have an inner diameter of preferably about 1 mm.

The distal mounting section 12 is cylindrical and is inserted detachably to the distal end of the first endoscope 27. The first endoscope is flexible endoscope. The distal mounting section 12 is made of a relatively soft plastic material such as PVC or other thermoplastic elastomer. Its inner diameter depends on the size of the distal end of the endoscope to be used and is generally about 10 mm.

The outer sheaths-connecting section 10 has a ring section fixed over the periphery of the distal cylindrical section 11, and connection legs 14a and 14b which are extending longitudinally and axially, parallel with each other. The connection legs 14a and 14b are preferably positioned at opposite sides and 180 degrees apart from one another. The connection legs 14a and 14b are preferably apart by 10 to 20 mm, depending on the outer diameter of the distal cylindrical section 11.

The connection legs 14a and 14b have penetration holes and form openings 15a and 15b at the distal end.

The outer sheaths 7a and 7b are hollow and flexible enough to follow the curvature of the first endoscope 27. For example, they are plastic tubes made of fluoroplastics, polyethylene, polyamide, polyimide, polyurethane or other thermoplastic elastomer, or metal coils. They may be metal coils covered by plastic tubes. They may be plastic tubes with metal mesh to prevent kink. The inner diameter is about 1 to 2 mm, the outer diameter is about 1.5 to 3 mm, and the length is about 1 to 1.5 m. The distal ends of the outer sheaths 7a and 7b are fixed to the connection legs 14a and 14b and are in parallel positions. The openings 15a and 15b are connected and communicated with the lumen of the outer sheaths 7a and 7b.

The operation section 9 comprises a base 16, grips 17a and 17b, sliders 18a and 18b, a proximal mounting section 20, and a channel port 21. The proximal ends of the outer sheaths 7a and 7b penetrate the base 16 and are connected to the distal ends of the grips 17a and 17b.

The grips 17a and 17b are cylindrical, and have screws 24a and 24b on the periphery of the proximal ends with which slider locks 22a and 22b are engaged. Between the screws 24a and 24b and the slider locks 22a and 22b, there are elastic tubular fixing rings 23a and 23b made of rubber such as silicon rubber or fluorine rubber, or thermoplastic elastomer. Sliders 18a and 18b are positioned slidably inside the fixing rings 23a and 23b. When the slider locks 22a and 22b are tightened, the fixing rings 23a and 23b are pressed longitudinally and expanded radially to immobilize the sliders 18a and 18b.

The sliders 18a and 18b are cylindrical. They are comprised of slider stoppers 25a and 25b at the proximal end for limiting a sliding area against the grips 17a and 17b, slider port 19a and 19b, and narrow sections 26a and 26b for connecting the inner sheaths-coupling member 5.

The proximal mounting section 20 is mounted at the distal end of the base 16, and is fixed detachably to a forceps channel port 28 of the first endoscope 27.

The channel port 21 is mounted to the proximal end of the base 16, and is plugged detachably with a forceps valve 29. The channel port 21 is connected through the lumen of the proximal mounting section 20 and the lumen in the base 16 to the forceps channel (not shown) of the first endoscope 27.

The inner sheath 3a or 3b comprises an inner sheath port 30, an inner sheath pipe 31, an O ring 32, and a sheath section 33. The inner sheath 3a or 3b can be inserted via the slider port 19 into the outer sheath 7.

When the inner sheath 3 is inserted to the outer sheath 7, the inner sheath port 30 is connected detachably to the slider port 19. The inner sheath port 30 has a lumen.

The inner sheath pipe 31 is connected to the sheath section 33 and the inner sheath port 30. The lumen of the inner sheath pipe 31 is also communicated with the lumen of the sheath section 33 and the lumen of the inner sheath port 30.

The O ring 32 is held between the proximal end of the inner sheath pipe 31 and the inner sheath port 30. It is made of elastic rubber such as silicon rubber or fluororubber, or thermoplastic elastomer. It is received in grooves 66a and 66b of a needle body 34 of the needle 4, which is described later, and stops movement of the needle body 34.

The sheath section 33 is hollow and flexible enough to follow the curvature of the first endoscope 27. For example, it is a plastic tube made of fluoroplastics, polyethylene, polyamide, polyimide, polyurethane or other thermoplastic elastomer, or a metal coil. It may be a plastic tube with metal mesh to prevent kink. The inner diameter is about 0.5 to 1.5 mm, and the outer diameter is about 1 to 2.5 mm.

When the slider 18 slides against the grip 17, The sheath section 33 slides in the outer sheath 7. The length of the inner sheath 3 is adjusted so that the distal end of the sheath section 33 is positioned proximal to the opening 15 when the slider 18 is pulled completely from the grip 17, and the distal end of the sheath section 33 is positioned distally about 15 to 50 mm from the opening 15 of the cap 8 when the slider 18 is pushed sufficiently to touch the grip 17.

The needle 4a or 4b comprises a needle body 34, a needle grip 35, and suture-holding forceps 38 inserted in them. The needle 4a or 4b can be inserted through the inner sheath port 30 into the inner sheath 3.

The needle body 34 is a metal pipe made of stainless steel or nitinol, which is resistant to pressure from the proximal end during piercing and flexible enough to follow the curvature of the first endoscope 27. The inner diameter is about 0.5 mm and the outer diameter is about 1 mm.

To facilitate projection of the distal end of the needle body 34 out of the distal end of the inner sheath 3, the outer diameter of the needle body 34 preferably approximates the inner diameter of the inner sheath 3. The proximal end of the needle body 34 is connected a port body 36 of the needle grip 35. The needle body 34 has two grooves 66a and 66b near the proximal end.

The needle body 34 slides in the inner sheath 3 by needle grip 35 moving back and forth against the inner sheath port 30. When the O ring 32 of the inner sheath 3 is engaged in the groove 66a, the distal end of the needle body 34 is positioned slightly proximal than the distal end of the sheath section 33, and when the O ring 32 is engaged in the groove 66b, the distal end of the needle body 34 extends out of the distal end of the sheath section 33. Preferably, the needle body 34 extends out of the distal end of the sheath section 33 by about 50 to 70 mm. Preferably, the distal ends of the needle bodies 34a and 34b should be apart by at least 10 mm when the needle bodies 34a and 34b extend out of the distal ends of the sheath sections 33a and 33b.

The needle grip 35 comprises a port body 36, a needle port 37, and a elastic cylindrical fixing ring 42 between them made of rubber such as silicon rubber or fluororubber, or thermoplastic elastomer.

The port body 36 and the needle port 37 have lumen and are connected with screws. An operation pipe 40 of the suture-holding forceps 38 slides in the lumen. When the needle port 37 is tightened, the fixing ring 42 is pressed longitudinally and expanded radially to fix the operation pipe 40. The needle port 37 also has a narrow section 43 to which the needles-coupling member 6 is connected.

The suture-holding forceps 38 is inserted in advance into the needle body 34 and the needle grip 35 for sliding. The suture-holding forceps 38 has a loop shaped holding section 41 at the distal end of the operation pipe 40. The holding section 41 is a metal wire made of stainless steel or nitinol, or plastic wire. The wire may be a single wire or a stranded wire. It has the diameter, which allows retracting the holding section 41 into the needle body 34. The holding section 41 is adjusted to open by 10 to 20 mm when it extends out of the needle body 34.

The holding section 41 can be of any loop shape. It may be like a basket forceps.

The operation pipe 40 extends from the proximal end of the holding section 41 to the proximal end of the needle port 37. The operation pipe 40 is connected an operation knob 39 at the proximal end. The operation pipe 40 is a slim metal pipe for smooth rotation such as stainless steel or nitinol. The holding section 41 is rotated following the rotation of the operation knob 39.

The inner sheaths-coupling member 5 can be mounted to the narrow sections 26a and 26b of the sliders 18a and 18b detachably.

The inner sheaths-coupling member 5 is an elastic yet relatively hard plastic sheet. There are two slits 44a and 44b on one side, which are connected to coupling holes 45a and 45b.

The width of the slits 44a and 44b are slightly narrower than the outer diameter of the narrow sections 26a and 26b of the sliders 18a and 18b. The inner diameter of the coupling holes 45a and 45b is nearly equal to the outer diameter of the narrow sections 26a and 26b. The each distance between the slits 44a and 44b, or coupling holes 45a and 45b is equal to the distance between the narrow sections 26a and 26b. When the slits 44a and 44b are pressed to the narrow sections 26a and 26b, the slits 44a and 44b open to connect the coupling holes 45a and 45b with the narrow sections 26a and 26b. To remove the inner sheaths-coupling member 5, the narrow sections 26a and 26b are pulled out of the slits 44a and 44b.

When the inner sheaths-coupling member 5 is mounted to the sliders 18a and 18b, both inner sheaths 3a and 3b can be moved back and forth at one time either by holding and moving one slider 18 or the inner sheaths-coupling member 5. The inner sheaths 3a and 3b extend by the same length out of the openings 15a and 15b.

To change the extension length of either inner sheath 3a or 3b, the inner sheaths-coupling member 5 is removed, and the sliders 18a and 18b are operated separately.

The needles-coupling member 6 and the inner sheaths-coupling member 5 are similarly composed. The needles-coupling member 6 can be mounted to the narrow section 43a and 43b of the needle ports 37a and 37b detachably. According to mounting and removing the needles-coupling member 6, the needles 4a and 4b are operated at one time or separately. When the separate operation is selected, the extension length of the needles 4a and 4b out of the distal end of the inner sheath 3a or 3b may be varied.

Figure 8:
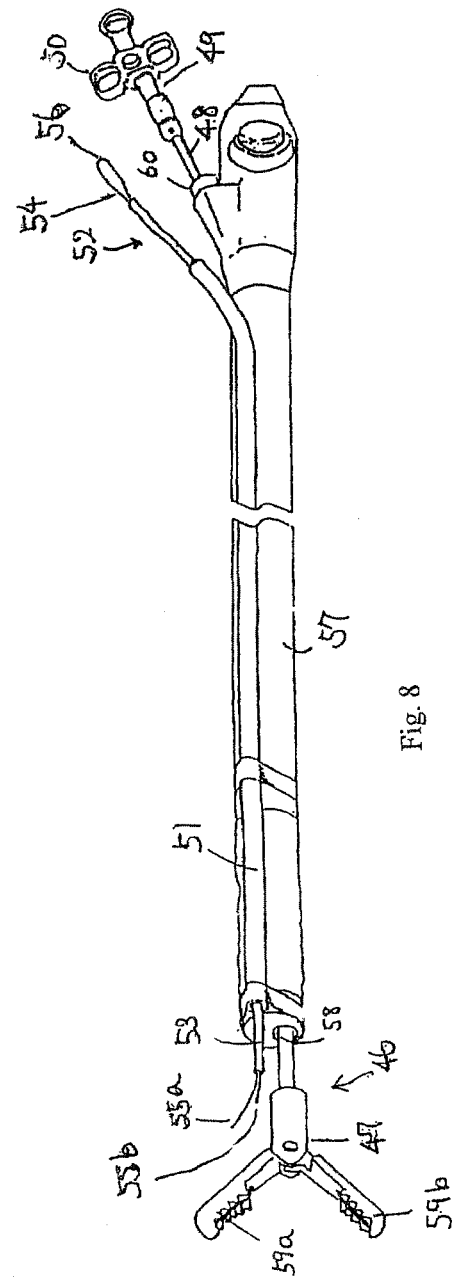
FIG. 8 shows a second endoscope having fixing-holding forceps inserted therethrough and a suture inserted through an outer channel fixed to the second endoscope.
Figure 9:
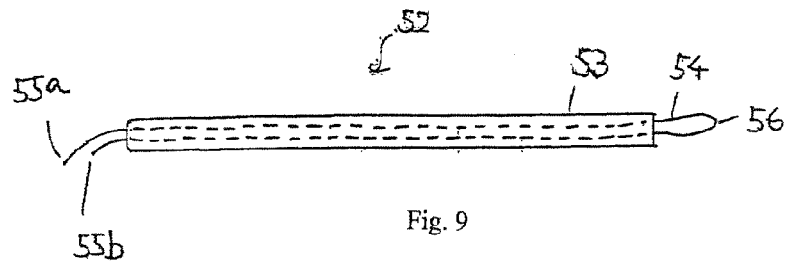
FIG. 9 shows a suture cartridge having a suture therein.

Description of the Fixing-Holding Forceps and a Suture (FIGS. 8 and 9)

The fixing-holding forceps 46 comprises a distal section 47, an elongate sheath 48 fixed at the proximal end of the distal section 47 and inserted in a forceps channel 58 of a flexible second endoscope 57, and an operation section 49 fixed detachably at the proximal end of the sheath 48 for operating the distal section 47.

The distal end section 47 has a pair of jaws 59a and 59b. The operation section 49 has a slider handle 50. An operation cable (not shown) connects the jaws 59a and 59b with the slider handle 50. The jaws 59a and 59b are opened or closed by moving the slider handle 50 back and forth.

The proximal end of the sheath 48 with the operation section 49 detached, is inserted from the distal opening of the forceps channel 58 through a forceps channel port 60. The operation section 49 is then mounted, and the fixing-holding forceps 46 is set on the second endoscope 57.

A suture cartridge 52 is inserted movably in the lumen of an outer channel 51 fixed on the outer periphery of the second endoscope 57.

The suture cartridge 52 comprises a hollow and flexible cartridge tube 53, and a suture placed in the hollow lumen. The cartridge tube 53 is made of plastic material such as fluoroplastics or polyethylene. The cartridge tube 53 is preferably made of relatively transparent material such as fluoroplastics so that the movement of the suture 54 is recognized easily in an endoscopic image.

The suture 54 is bent at the proximal end of the cartridge tube 53 and is stored, movably, in a U-shape in the cartridge tube 53. The fold 56 is exposed out of the proximal end of the cartridge tube 53. Suture ends 55a and 55b are exposed out of the distal end of the cartridge tube 53. At that point, the suture ends 55a and 55b are positioned so that one is 5 to 10 mm in front of the other. The suture 54 is a general surgical suture made of, for example, nylon or silk. The suture 54 is 0.2 to 0.5 mm thick, and preferably 0.3 to 0.4 mm thick. The suture ends 55a and 55b are preferably colored differently for easy recognition: A part from the suture end 55a to the fold 56 is colored differently from a part from the suture end 55b to the fold 56, and the two parts are welded at the fold 56.

Figure 10:
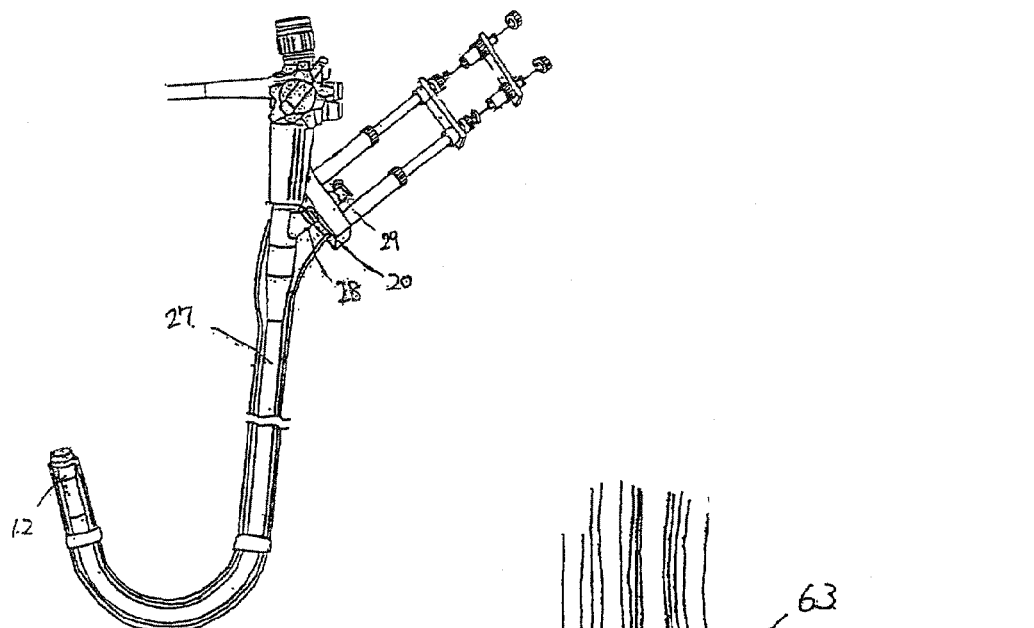
FIG. 10 shows the piercing device according to the first embodiment mounted to a first endoscope.

Mounting the Device to an Endoscope (FIGS. 8 and 10)

The piercing device 1 is mounted in the following procedure.

The proximal mounting section 20 is mounted to the forceps channel port 28 of the first endoscope 27. The distal mounting section 12 of the cap 8 is inserted to the distal end of the first endoscope 27 while the outer sheaths 7a and 7b are held lest they should be twisted. The outer sheaths 7a and 7b are fixed at several points on the outer periphery of the first endoscope 27 with surgical tape.

The inner sheaths 3a and 3b are inserted through the slider ports 19a and 19b to the outer sheaths 7a and 7b, and the inner sheath port 30a and 30b are connected and fixed to the slider ports 19a and 19b.

With the suture-holding forceps 38a and 38b placed completely into the needle bodies 34a and 34b, the needles 4a and 4b are inserted through the inner sheath ports 30a and 30b into the inner sheaths 3a and 3b. The groove 66a of the needle bodies 34a and 34b should be engaged with the O ring 32 of the inner sheaths 3a and 3b. The needle bodies 34a and 34b are then positioned so as not to extend out of the distal ends of the sheath sections 33a and 33b.

The sliders 18a and 18b are pulled proximally. The sheath sections 33a and 33b are pulled in the outer sheaths 7a and 7b in advance so that the distal ends of the sheath sections 33a and 33b are positioned more proximally than the openings 15a and 15b.

The fixing-holding forceps 46 is mounted to the second endoscope 57 in advance.

Figure 11:
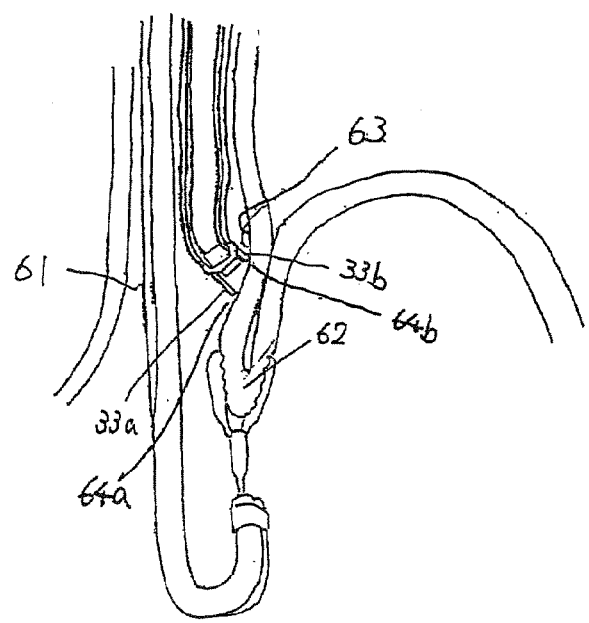
FIG. 11 shows grasping the cardia with fixing-holding forceps via the second endoscope and inserting the first endoscope to a piercing position.

Holding and Pulling Down the Cardia (FIG. 11)

The sheath 48 of the fixing-holding forceps 46 is pulled proximally and retained in a position in which the distal section 47 preferably does not extend out of the distal end of the second endoscope 57. The second endoscope 57 is inserted into the patient's body, advanced to the stomach, and inverted to look up at the cardia 61 for observation.

Next, the slider handle 50 is pushed out against the operation section 49 distally to open the jaws 59a and 59b. The sheath 48 is sent toward the distal end, and the jaws 59a and 59b are brought into contact with tissue of the greater curvature 62 of the cardia 61. The slider handle 50 is then pulled proximally to close the jaws 59a and 59b and hold and fix the tissue 62.

The second endoscope 57 and the fixing-holding forceps 46 are pressed together into the patient's body and pulled down while the tissue 62 is held and fixed between the jaws 59a and 59b.

When a valve to be formed is not so large, the cardia may not be held and pulled down by the fixing-holding forceps 46.

Figure 12:
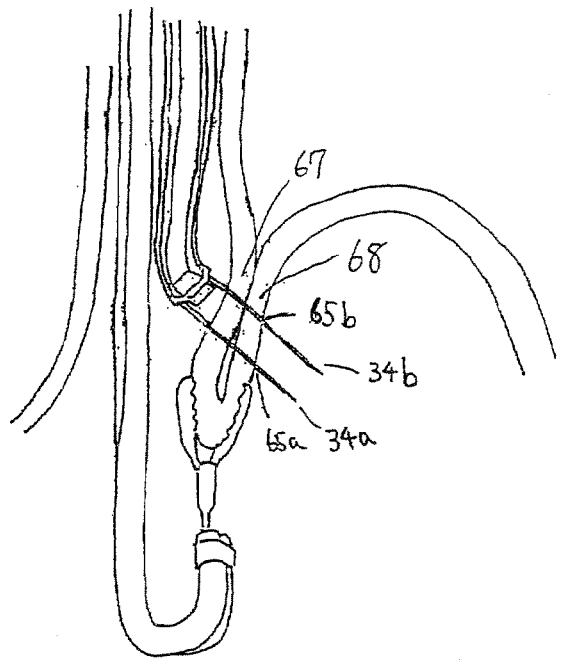
FIG. 12 shows piercing of the esophageal and gastric walls with the piercing device of the first embodiment.
Figure 13:
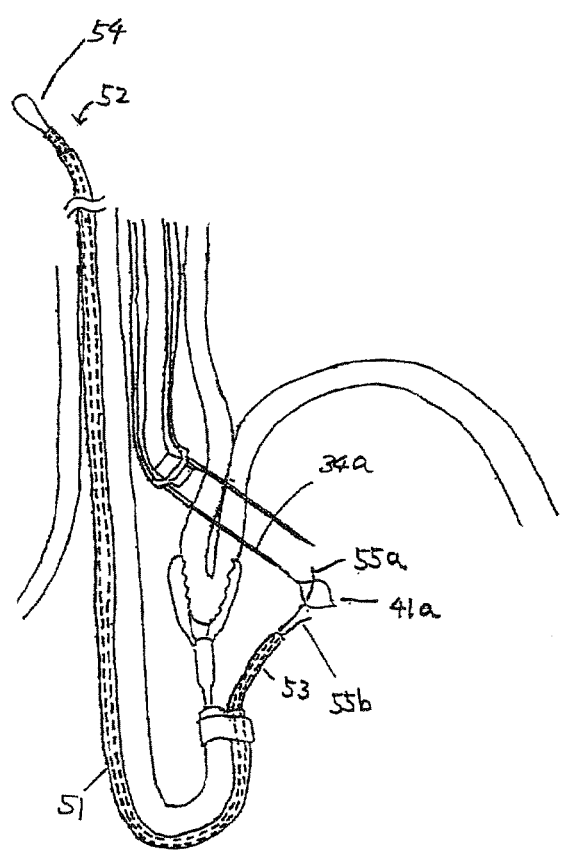
FIGS. 13-16 show insertion of a suture into the pierced tissue according to the first embodiment.
Figure 14:
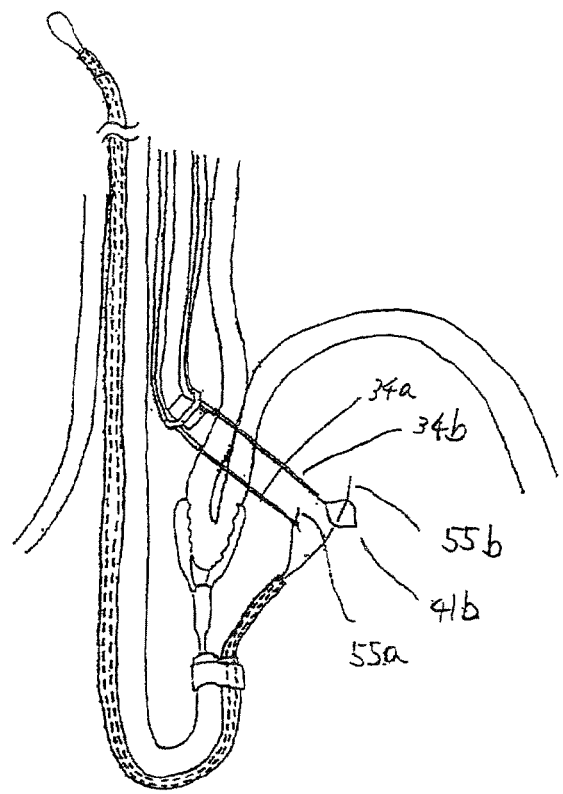
Figure 15:
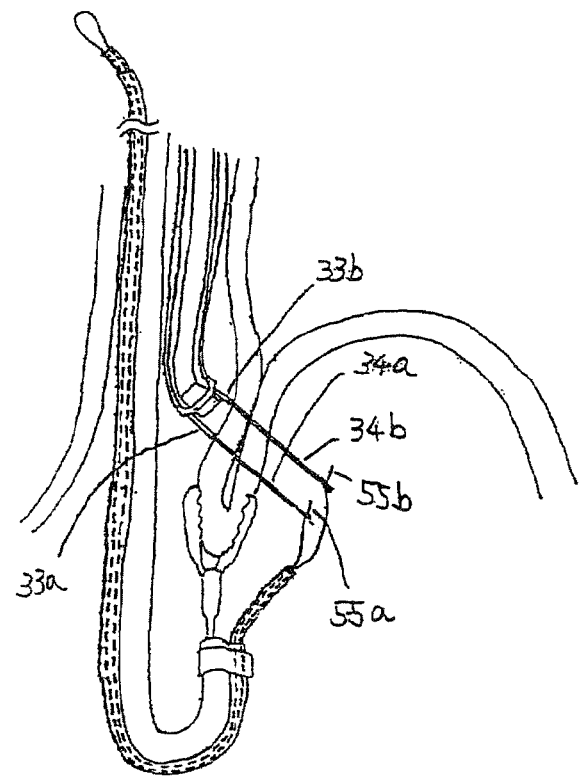
Figure 16:
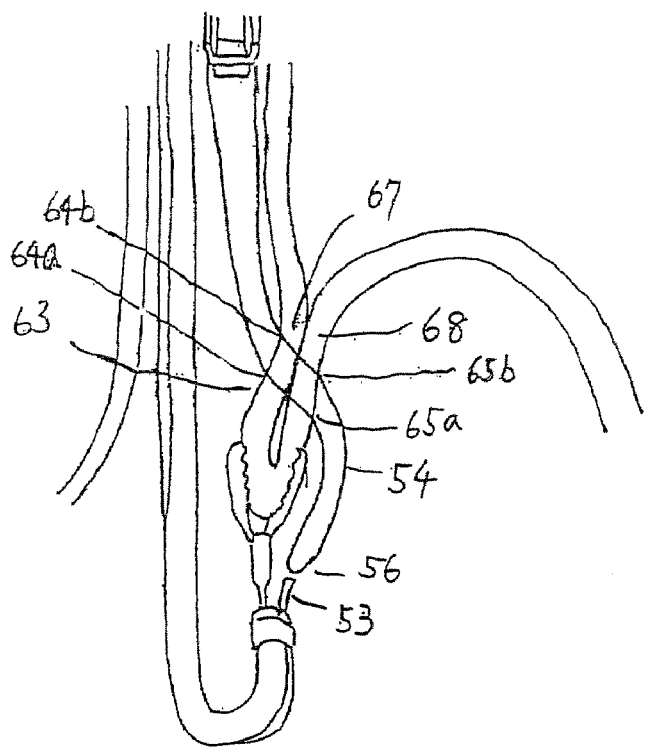

Penetrating the Stomach and the Esophagus Using a Penetration Needle (FIGS. 11 and 12)

The first endoscope 27 is inserted parallel to the second endoscope 57. The distal end of the first endoscope 27 is positioned at an upstream point 63 of the esophagogastric junction while they are observed. The distal end of the first endoscope 27 is inclined slightly toward the greater curvature of the stomach. The sliders 18a and 18b are moved against the grips 17a and 17b to the distal end. The sheath sections 33a and 33b are extended out of the openings 15a and 15b and pressed against the entering points 64a and 64b. Depending on the condition and form of the body lumen, the inner sheaths-coupling member 5 is either attached to the narrow sections 26a and 26b to press the sheath sections 33a and 33b at one time, or is removed to press the sheath sections 33a and 33b separately.

After the sheaths sections 33a and 33b are pressed, the slider locks 22a and 22b are tightened to the grips 17a and 17b to fix the sliders 18a and 18b.

The needle grips 35a and 35b are pressed toward the distal end until the groove 66b of the needle bodies 34a and 34b is engaged with the O ring 32, and the needle bodies 34a and 34b are extended out of the sheath sections 33a and 33b.

The needles-coupling member 6 is either attached to the narrow sections 43a and 43b to press the needle bodies 34a and 34b at one time, or is removed to press the needle bodies 34a and 34b separately. Pressing the needle bodies 34a and 34b at one time makes operation easy, but increases penetration resistance of the needles and requires more force to penetrate them into tissue. On the other hand, pressing the needle bodies 34a and 34b separately makes it easy to penetrate the tissue, but requires two rounds of penetration procedures.

When the needle bodies 34a and 34b are extended out of the sheath sections 33a and 33b, they pass through the entering points 64a and 64b of the esophageal wall 67, the exiting points 65a and 65b of the stomach wall 68 near the cardia and enter the stomach.

The second endoscope 57 is used to check that the needle bodies 34a and 34b enter the stomach.

Inserting a Suture to Tissue (FIGS. 13 to 16)

The suture cartridge 52 is inserted into the outer channel 51 and extended into the stomach while it is observed by the second endoscope 57. The operation knob 39a of the needle 4a is pressed toward the distal end and the holding section 41a is extended out of the distal end of the needle body 34a.

Either the suture cartridge 52 or the suture 54 is advanced or retreated to insert the suture end 55a into the holding section 41a.

Because the holding section 41a is synchronized and rotated with the operation knob 39a, it is easy to insert the suture end 55a into the holding section 41a.

The operation knob 39a is pulled proximally to pull the holding section 41a into the needle body 34a and hold the suture end 55a.

The needle port 37a of the needle grip 35a is tightened to the port body 36a to lock the holding section 41a and the suture end 55a.

Similarly, the suture end 55b is held by the holding section 41b.

Since the holding sections 41a and 41b are loop shape, they can prevent that the suture 54 slips from the holding sections 41a and 41b. As a result, it is easy to hold the suture 54 by the holding sections 41a and 41b.

The needle grips 35a and 35b are then pulled back proximally and the distal ends of the needle bodies 34a and 34b are pulled into the sheath sections 33a and 33b. The suture ends 55a and 55b penetrate the gastric wall 68 and the esophageal wall 67 and reach to the upstream point 63 of the esophagogastric junction.

The slide locks 22a and 22b are loosened, and the grips 18a and 18b are pulled back proximally to pull the distal ends of the sheath sections 33a and 33b in the outer sheaths 7a and 7b. The first endoscope 27 is then removed from the patient's body. The suture 54 is drawn out of the cartridge tube 53.

After the first endoscope 27 and the piercing device 1 are removed from the patient's body, the operation knobs 39a and 39b are pressed toward the distal end to extend the holding sections 41a and 41b out of the outer sheaths 7a and 7b, and remove the suture ends 55a and 55b out of the holding sections 41a and 41b.

The suture ends 55a and 55b are pulled further to bring the fold 56 into contact with the inner surface of the gastric wall 68.

The slider handle 50 of the fixing-holding forceps 46 is then moved toward the distal end to open the jaws 59a and 59b and release the tissue 62. The second endoscope 57 is removed together with the fixing-holding forceps 46 and the cartridge tube 53.

Figure 17:
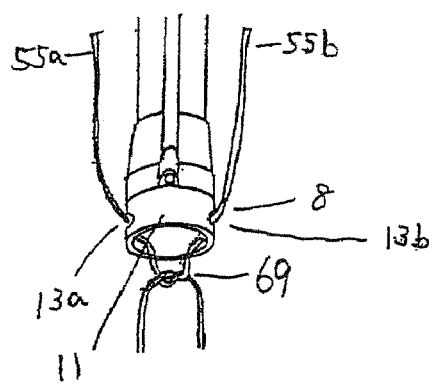
FIGS. 17-19 show fixing the suture and forming an artificial valve according to the first embodiment.
Figure 18:
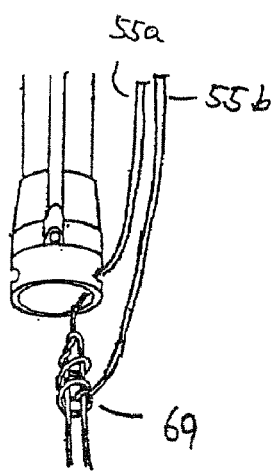
Figure 20:
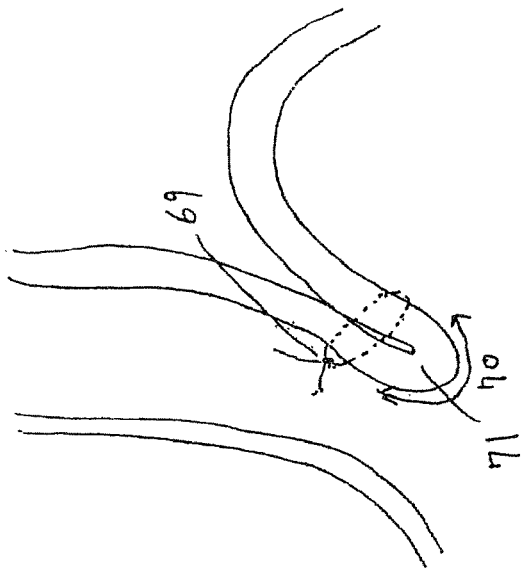
FIG. 20 shows the suture fixed in place.
Figure 19:
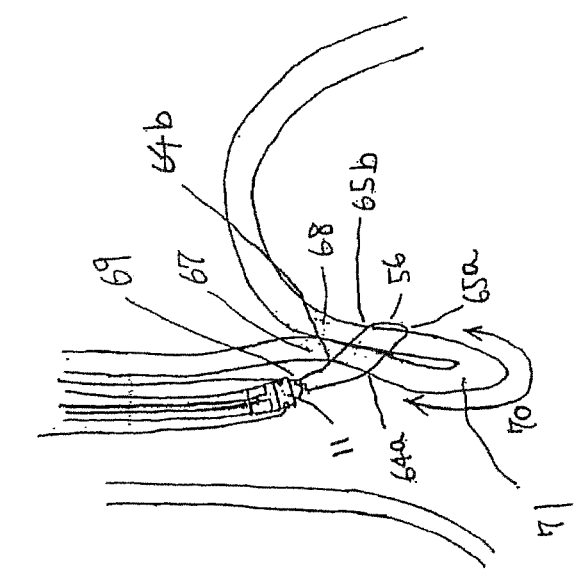
Figure 21:
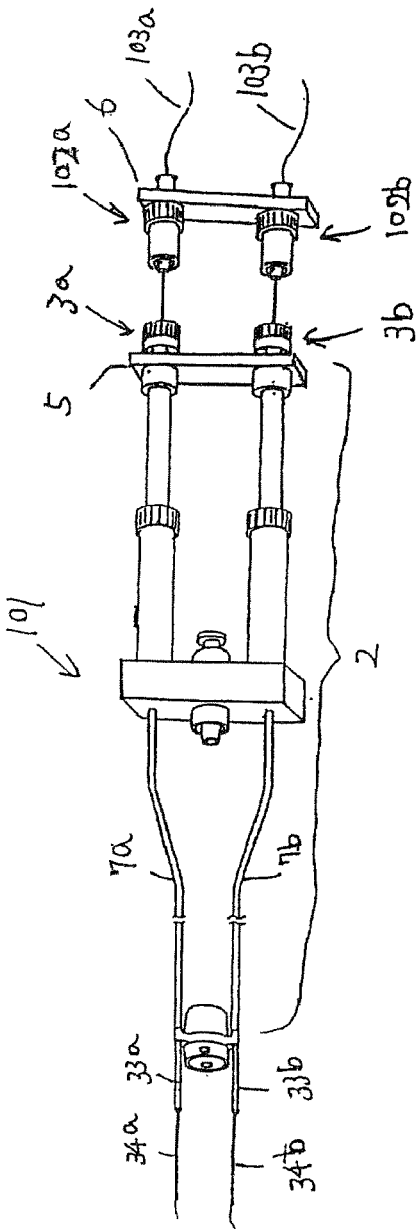
FIG. 21 shows a piercing device according to a second embodiment of the present invention.
Figure 22:
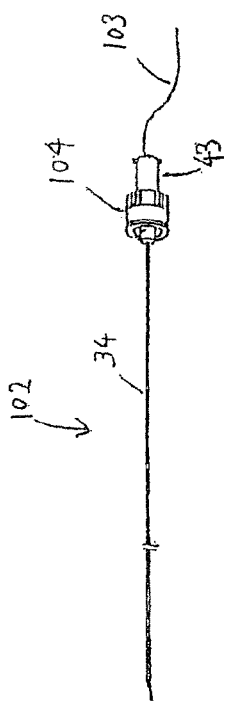
FIG. 22 shows a needle according to the second embodiment.
Figure 23:
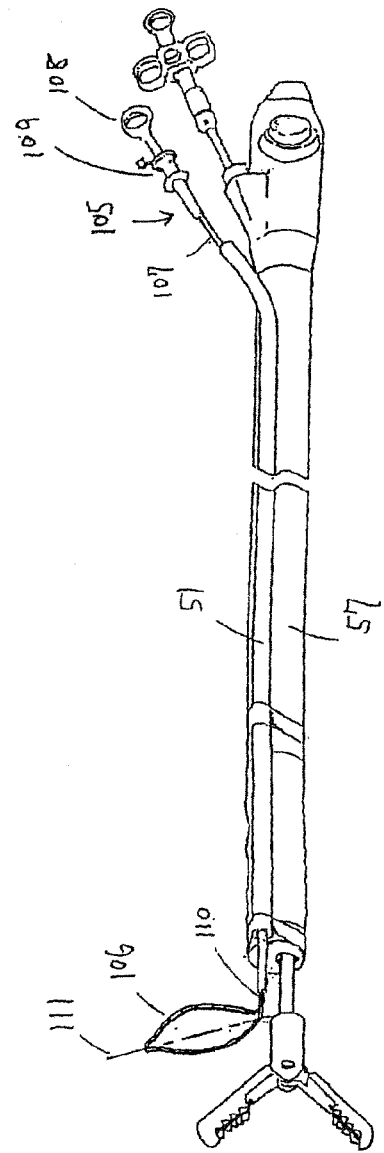
FIG. 23 shows a second endoscope having fixing-holding forceps inserted therethrough and suture-holding forceps inserted through an outer channel fixed to the second endoscope.
Figure 24:
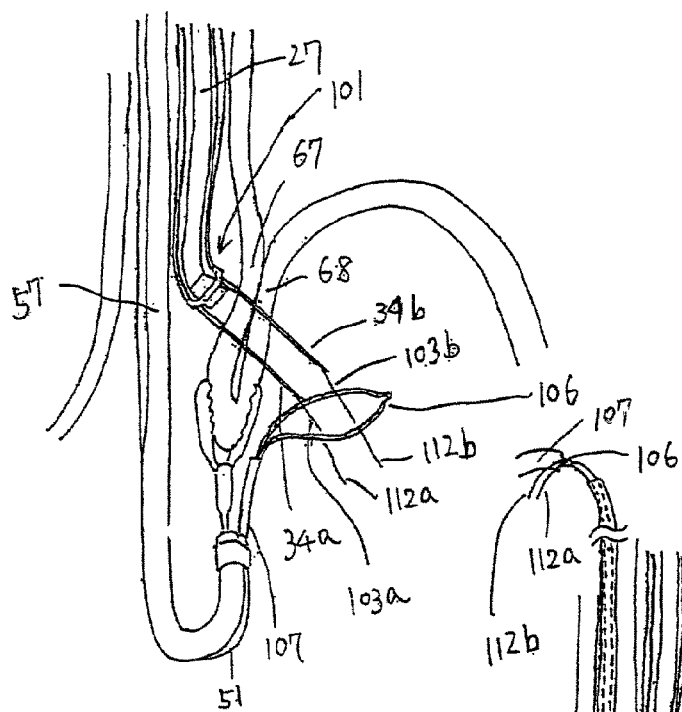
FIG. 24 shows grasping the cardia with fixing-holding forceps via the second endoscope, piercing the esophageal and gastric walls with the piercing device according to the second embodiment via the first endoscope and inserting two sutures, and capturing the two sutures with a holding section via the second endoscope.
Figure 25:
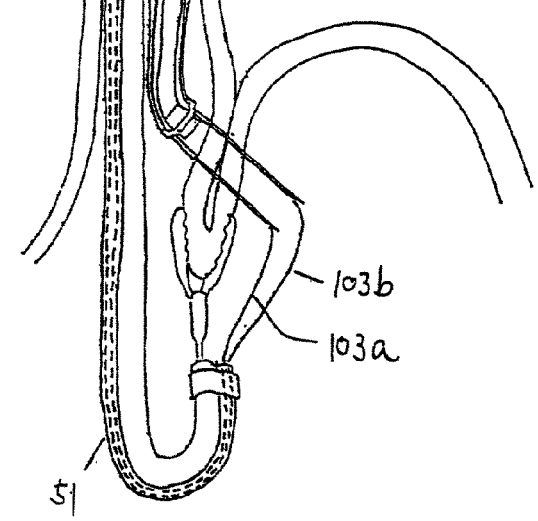
FIGS. 25-27 show tying a knot in the sutures according to the second embodiment of the present invention.
Figure 26:
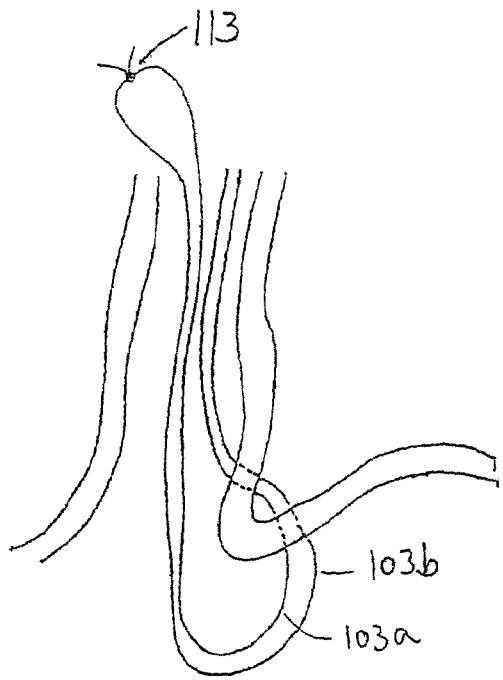
Figure 27:
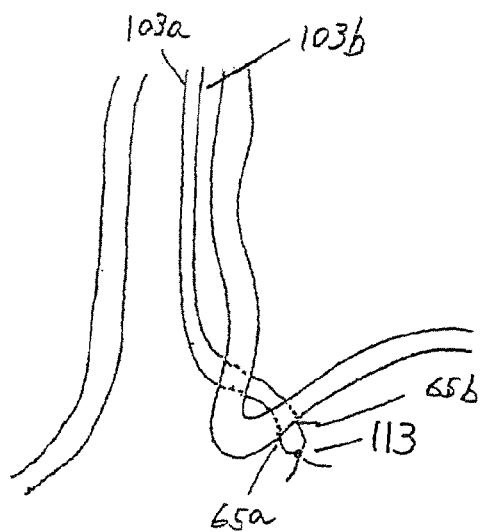

Fixing the Suture and Forming an Artificial Valve (FIGS. 17 to 19)

The suture ends 55a and 55b are tied outside the patient's body to form a knot 69.

If the knot 69 is a so-called square knot as shown in FIG. 17, the suture ends 55a and 55b are inserted into the side holes 13a and 13b at the distal cylindrical section 11 of the cap 8.

If the knot 69 is a so-called Roeder knot as shown in FIG. 18, only one suture end 55a is inserted into the side hole 13a or 13b.

The suture ends 55a and 55b are inserted in a way that they pass the inner to the outside of the distal cylindrical section 11.

The first endoscope 27 is advanced into the patient body while the suture ends 55a and 55b are held and pulled.

The knot 69 is advanced by the distal cylindrical section 11 of the cap 8 as the first endoscope 27 is inserted. The knot 69 can be observed by the first endoscope 27.

When the knot reaches near the entering points 64a and 64b of the esophagus, the distal cylindrical section 11 is pressed against the esophageal wall 67, while the suture ends 55a and 55b are pulled to lock the knot 69.

The above procedure is repeated several times before it is checked that the knot 69 is tied firmly. Then the first endoscope 27 and the piercing device 1 are removed from the patient's body.

As a result, the gastric wall near the exiting points 65a and 65b is brought close to the entering points 64a and 64b. The esophagogastric junction 70 between the exiting points 65a and 65b and the entering points 64a and 64b are contracted to form an inward projection 71.

Finally, excess sutures beyond the knot 69 are cut using endoscopic scissors, and are collected outside the body to finish the treatment.

The fixing-holding forceps 46 inserted in the second endoscope 57 allow pulling the tissue 62 while it is held and fixed.

The jaws 59a and 59b are brought into contact with the tissue 62 under observation using the second endoscope 57, which simplifies operation and shortens its time.

Because the first endoscope 27 and the piercing device 1 which are operated separately from the second endoscope 57 and the fixing-holding forceps 46 are provided, the pulling amount of the cardia or the position of the entering point 64 can be determined at an operator's discretion to form a valve of any size, depending on the condition of a particular patient.

The piercing device 1 incorporates two penetration needles in advance, so once the distal end of the first endoscope 27 approaches a penetration point of the esophageal wall 67, two needles can be penetrated immediately. This also means easy operation and reduced time.

The piercing device 1 has the sheath sections 33a and 33b and the distal end of them can be touched body tissue before shooting the needle bodies 34a and 34b. It makes it easy to locate the penetration point and reliably penetrates toward the inside of the stomach through the esophagogastric junction 70. If a larger valve is not required, such a valve can be formed with no tissue 62 held and fixed by the fixing-holding forceps 46. It simplifies operation and shortens the time.

The piercing device 1 has two penetration needles in parallel, so the entering points 64a and 64b and the exiting points 65a and 65b are set apart a desired distance. As a result, an area of the body tissue to be contracted by the suture is not small but still large enough to form a valve of desired size.

The outer sheaths 7a and 7b which receive the needles 4a and 4b are attached to the cap 8 at a desired position. Only by attaching the cap 8 to the distal end of the first endoscope 27, can the distal ends of the outer sheaths 7a and 7b be mounted easily to the distal end of the first endoscope 27 at a specified position. This shortens the time required for mounting to the endoscope.

The side holes 13a and 13b on the cap 8 are capable of holding and pushing the knot of the suture. It is not necessary to prepare a knot pusher for holding and pushing the knot, which decreases medical costs and eliminates the need for another tool.

The needles 4a and 4b can be housed in the inner sheaths 3a and 3b and the outer sheaths 7a and 7b. The piercing device 1 is inserted into a body lumen without damaging it.

Second Embodiment (FIGS. 21 to 27)

Only points which are different from those of the first embodiment are described.

A piercing device 101 is the piercing device 1 with its needles 4a and 4b replaced by needles 102a and 102b.

The needle 102 comprising a needle body 34, a needle grip 104 connected proximal to the needle body 34, and a suture 103 inserted movably in the needle body 34 and the needle grip 104. The needle grip 104 has a narrow section 43 to which the needles-coupling member 6 is connected.

The lumen in the outer channel 51 fixed on the outer periphery of the second endoscope 57 has suture-holding forceps 105 which are inserted movably.

The suture-holding forceps 105 comprise a flexible sheath 107, an operation section 108 which is rotated against and connected proximal to the flexible sheath 107, a handle 109 which slides against the operation section (108), a driving member 110 which is connected at the distal end of the handle 109 and extended slidably in the sheath 107, and a holding section 106 connected at the distal end of the driving member 110. The holding section 106 is extended out or withdrawn into the distal end of the sheath 107 by moving the handle 109 back and forth.

The holding section 106 can be of any loop shape, for example, snare forceps or basket forceps. The holding section 106 is a metal wire made of stainless steel or nitinol, or a plastic wire. The wire can be a single wire or strand wire. The wire is thick enough to pull the holding section 106 into the sheath 107. The holding section 106 is so sized as to open by 10 to 30 mm when it is extended out of the sheath 107.

The holding section 106 is bent and mounted to the driving member 110 so that the central axis 111 of the loop forming the holding section 106 inclines against the longitudinal direction of the driving member 110.

The driving member 110 is made of a metal wire that follows any rotation. The holding section 106 rotates following the operation section 108.

After the needle bodies. 34a and 34b of the piercing device 101 mounted to the first endoscope 27 pierce the esophageal wall 67 and the gastric wall 68, the suture-holding forceps 105 are inserted into the outer channel 51 fixed on the outer periphery of the second endoscope 57 to introduce the distal end of the sheath 107 in the stomach under observation using the second endoscope 57.

The handle 109 is pressed toward the distal end to extend the holding section 106 out of the sheath 107.

The sheath 107 is moved back and forth, or the operation section 108 is rotated, to rotate the holding section 106 and position it just below the needle bodies 34a and 34b. The sutures 103a and 103b inserted in the needles 102a and 102b are pressed and inserted in the loop of the holding section 106.

The handle 109 is then pulled proximally to pull the holding section 106 in the sheath 107 and hold and fix the suture ends 112a and 112b of the sutures 103a and 103b.

The suture-holding forceps 105 are removed from the outer channel 51 while fixing the suture ends 112a and 112b.

The holding section 106 is opened again to remove the suture ends 112a and 112b. They are tied to form a knot 113, and the excess sutures are cut off. The sutures 103a and 103b exposing proximally beyond the needle grip 104a and 104b of the needles 102a and 102b are pulled to pull the knot 113 back into the patient's body. The knot 113 should touch near the exiting points 65a and 65b of the stomach.

In addition to the effect of the first embodiment, because the holding section 106 of the suture-holding forceps 105 holds the suture ends 112a and 112b at one time, suture-holding operations using the suture-holding forceps in the body are halved, simplifying operation and reducing time.

Figure 28:
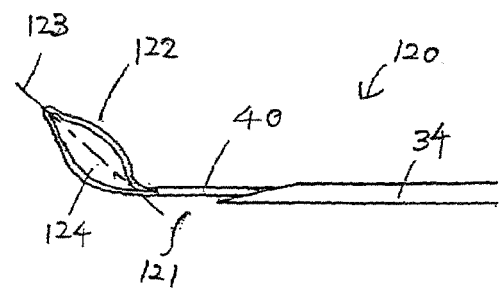
FIG. 28 shows a needle and suture-holding forceps according to a third embodiment of the present invention.
Figure 29:
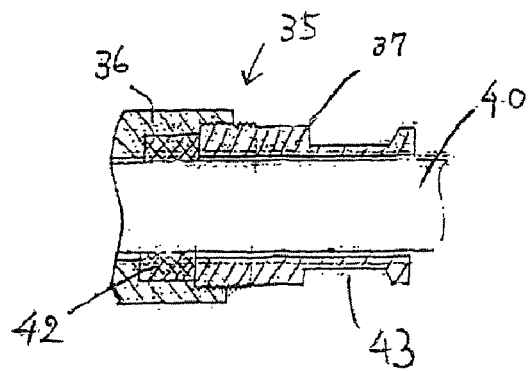
FIG. 29 shows a cross-sectional view of a needle grip according to the first embodiment.
Figure 30:
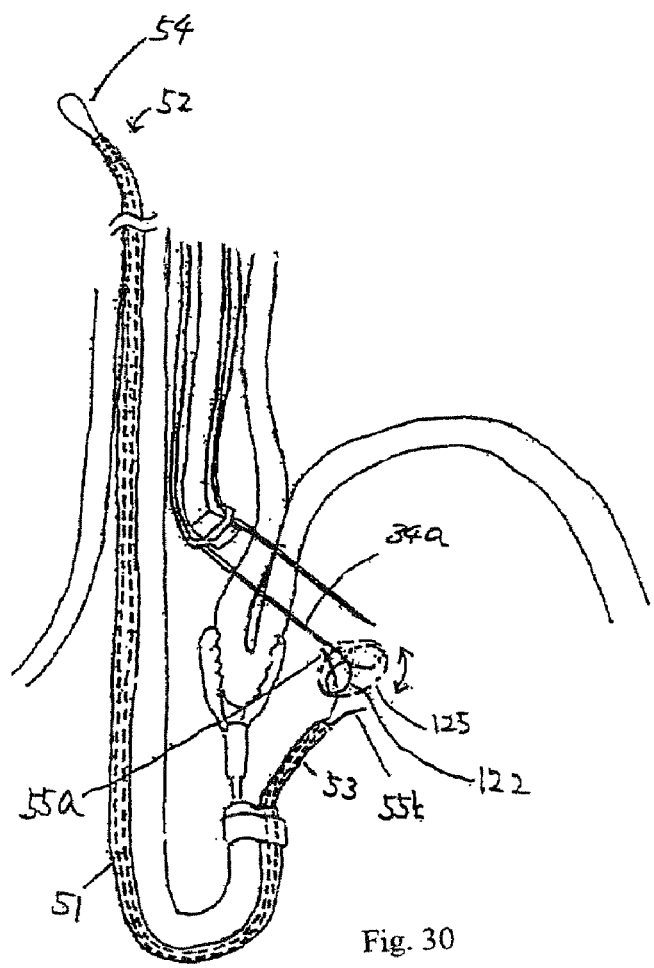
FIG. 30 shows the suture-holding forceps of the third embodiment in use to capture a suture.

Third Embodiment (FIGS. 28 and 30)

Only points which are different from those of the first embodiment are described.

The suture-holding forceps 121 of the needle 120 have a holding section 122 at the distal end of the operation pipe 40. The holding section 122 is bent and mounted to the operation pipe 40 so that the central axis 123 of the loop 124 forming the holding section 122 inclines against the longitudinal axis of the operation pipe 40.

When the holding section 122 is rotated, the loop 124 forming the holding section 122 is moved in an area 125 larger than that of the first embodiment.

Because the loop 124 forming the holding section 122 moves in a larger area, the suture-end is inserted into the loop 124 easily for improved operability and shortened time.

Figure 31:
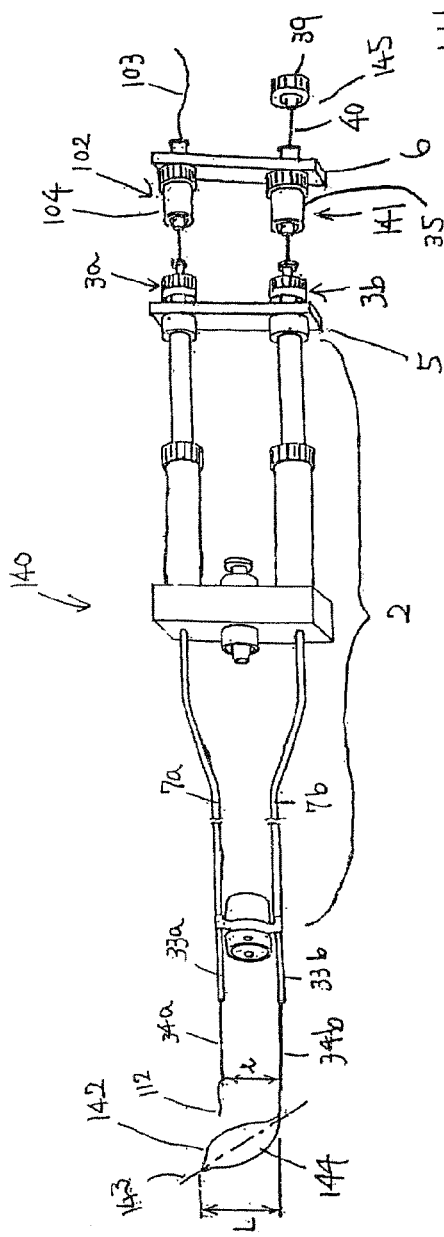
FIG. 31 shows a piercing device according to a fourth embodiment of the present invention.
Figure 32:
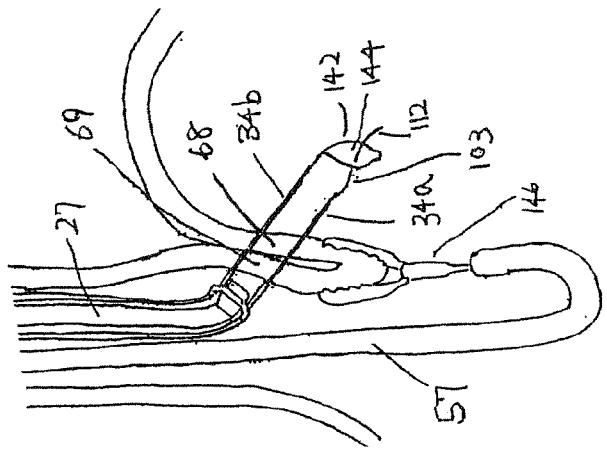
FIGS. 32 and 33 show the piercing device of the fourth embodiment in use to form an artificial valve.
Figure 33:
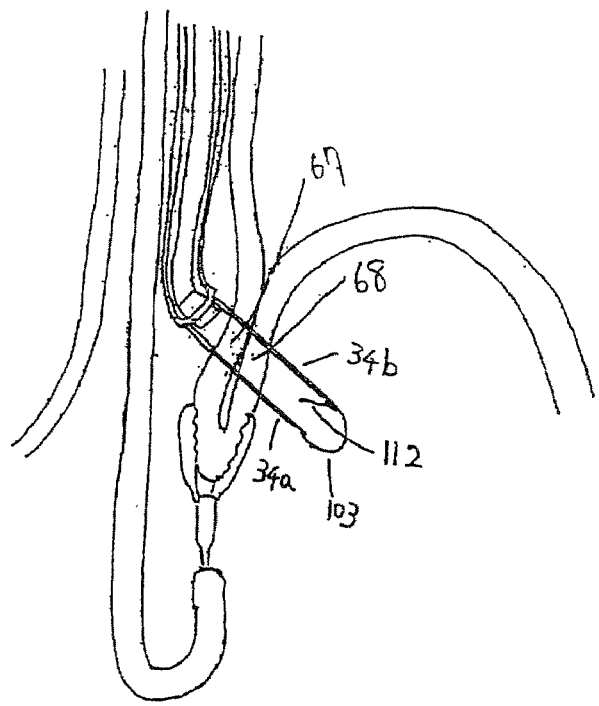

Fourth Embodiment (FIGS. 31 to 33)

Only points which are different from those of the first embodiment are described.

A piercing device 140 is the piercing device 1 with one of the needles 4a and 4b replaced by the needle 102 in the second embodiment, and the other replaced by a needle 141. The needle 102 is comprised same with that of the second embodiment.

Suture-holding forceps 145 that extend from or retract into the needle 141 have a holding section 142 at the distal end of the operation pipe 40. The holding section 142 is bent and mounted to the operation pipe 40 so that the central axis 143 of the loop 144 forming the holding section 142 inclines against the longitudinal axis of the operation pipe 40.

The length L of the holding section 142 is longer than the distance I between the two needle bodies 34a and 34b, and the suture end 112 of the suture 103 extending out of the needle 102 is inserted in a loop 144 formed by the holding section 142.

The second endoscope 57 does not have the outer channel 51, and the fixing-holding forceps 46 are inserted in a forceps channel (not shown).

After the needle bodies 34a and 34b of the piercing device 140 which are mounted to the first endoscope 27 pierce the esophageal wall 67 and the gastric wall 68, the holding section 142 of the suture-holding forceps 145 is extended out of the needle 34b.

The operation knob 39 is rotated while it is observed by the second endoscope 57 to rotate the holding section 142 until the longitudinal axis of the needle body 34a is positioned in the loop 144 of the holding section 142.

The suture 103 in the needle 102 is pressed out, and the suture end 112 is inserted in the loop 144.

The operation knob 39 is pulled proximally to hold the suture end 112.

Next, with the suture 103 extending from the proximal end of the needle grip 104 released, the needle grips 35 and 104 are pulled back proximally to retract the distal ends of the needle bodies 34a and 34b into the sheath sections 33a and 33b. Thus, the suture end 103 penetrates the gastric wall 68 and the esophageal wall 67.

The suture is penetrated only with the piercing device 140 and another device such as suture-holding forceps is not necessary. Preparation before treatment is simplified and does not take a long time. Moreover, another tool is not necessary and the cost is reduced.

Because the second endoscope 57 does not require the outer channel 51, the second endoscope 57 is narrowed and inserted into a body lumen easily.

Figure 34:
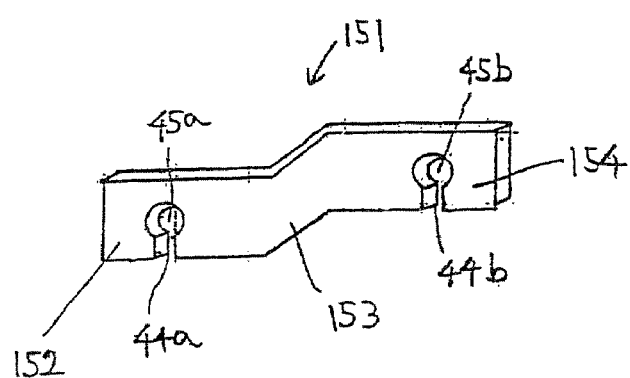
FIG. 34 shows a needles-coupling member according to a fifth embodiment of the present invention.
Figure 35:
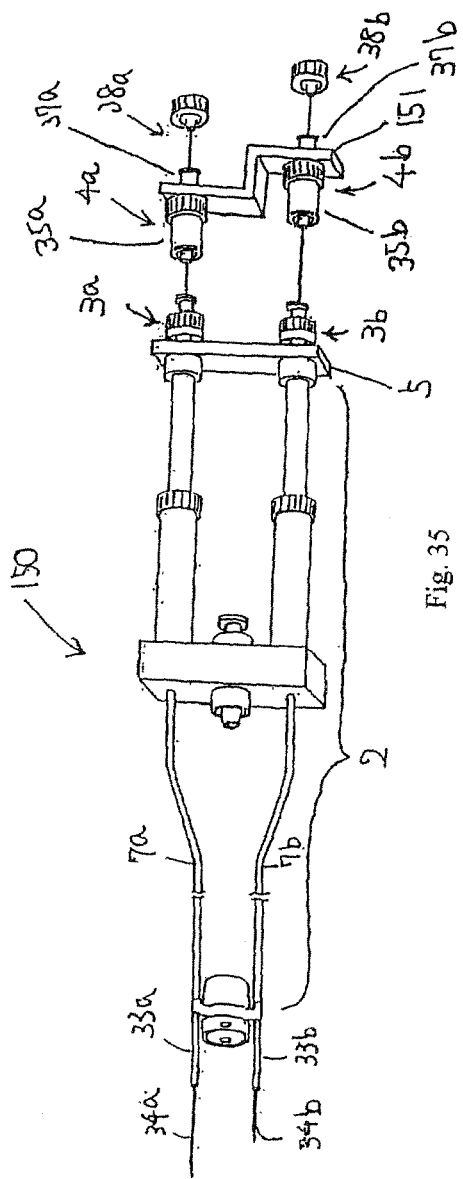
FIG. 35 shows a piercing device according to the fifth embodiment.
Figure 36:
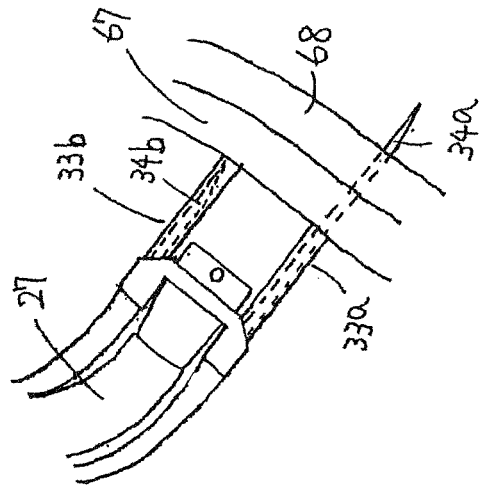
FIG. 36 shows esophageal and gastric walls being pierced by the piercing device of the fifth embodiment.
Figure 39:
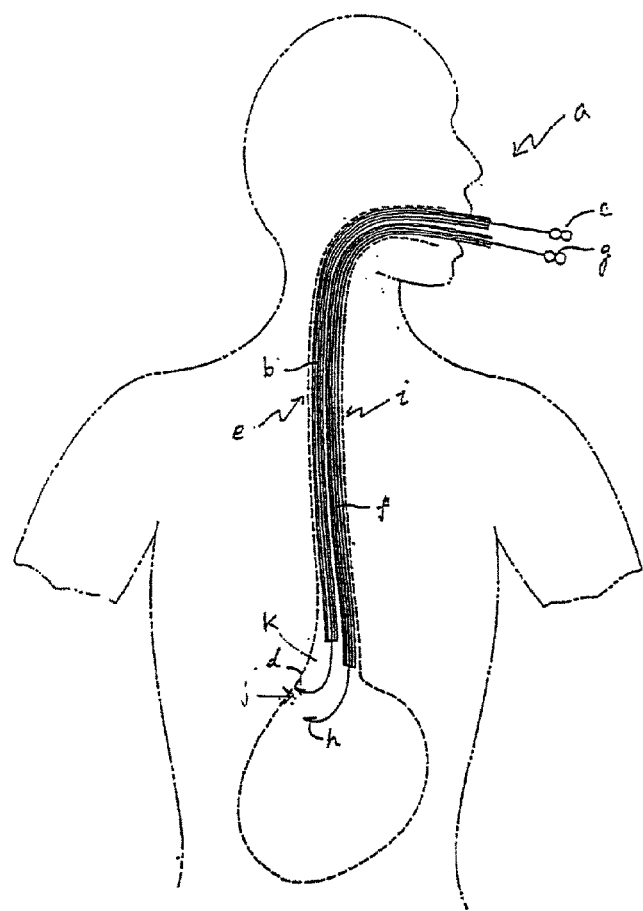
FIG. 39 shows a tool for transoral treatment of GERD according to U.S. Pat. No. 5,887,594.
Figure 40:
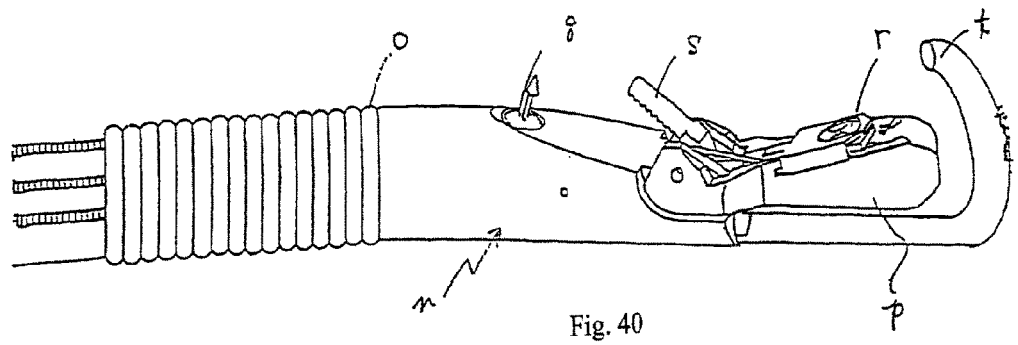
FIGS. 40-44 show a tool for transoral treatment of GERD according to WO 99/22649.
Figure 41:
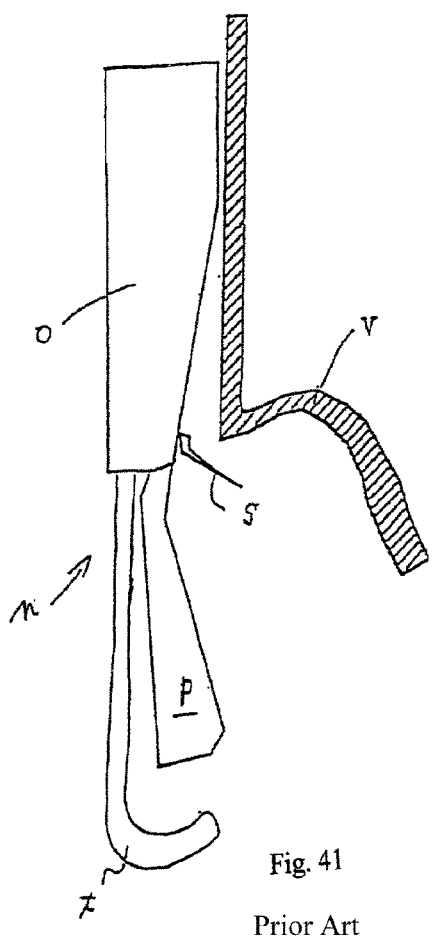
Figure 42:
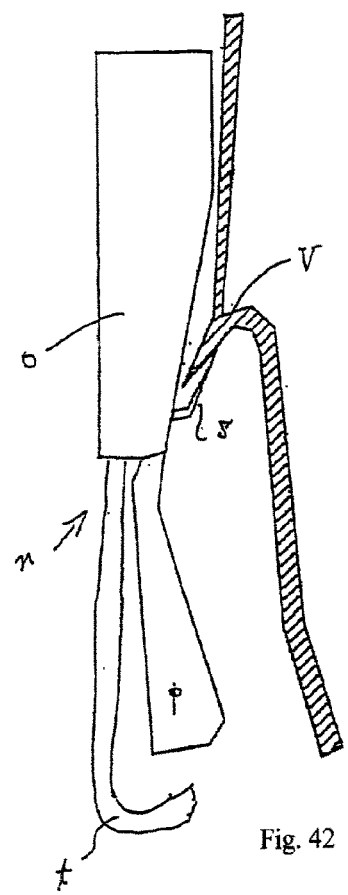
Figure 43:
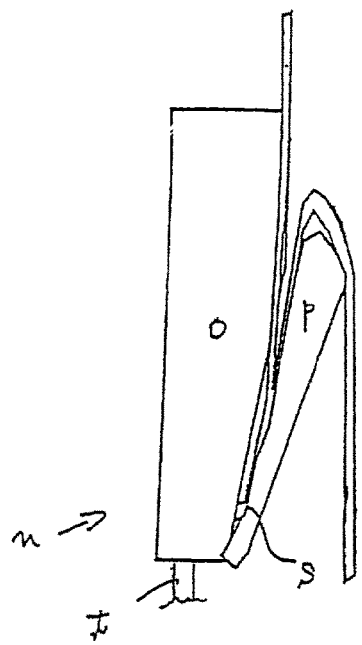
Figure 44:
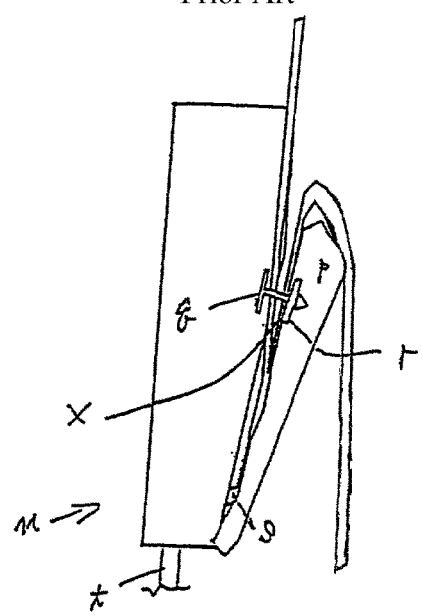

Fifth Embodiment (FIGS. 34 to 36)

Only points different from those of the first embodiment are described.

A piercing device 150 is the piercing device 1 with the needles-coupling member 6 replaced by a needles-coupling member 151.

The needles-coupling member 151 comprising a distal section 152, a middle section 153 and a proximal section 154, and is shaped like a crank. The distal section 152 and the proximal section 154 are positioned longitudinally apart each other. The distal section 152 should be apart from the proximal section 154 by at least the thickness of tissue to be penetrated, or at least 5 mm.

Coupling holes 45a and 45b of the needles-coupling member 151 are mounted via the slits 44a and 44b to the needle ports 37a and 37b of the needle grips 35a and 35b. Because the distal section 152 and the proximal section 154 are apart each other, the distal ends of the needle bodies 34a and 34b are longitudinally apart from each other. When the needles-coupling member 151 is held and pressed toward the distal end, the needle bodies 34a and 34b are extended out of the inner sheaths 33a and 33b with its distance between the two maintained.

When the piercing device 150 is used for penetrating the esophageal wall 67 and the gastric wall 68, first needle body 34a penetrates the esophageal wall 67 and the gastric wall 68; next needle body 34b penetrates them.

Because two needles never penetrates tissue at one time even if the needles coupling-member 151 is pressed to operate the two needles, penetration resistance will not be increased, and penetration is easy.

Sixth Embodiment (FIGS. 37 and 38)

Only points that are different from those of the fixing-holding forceps 46 in the first embodiment are described.

As shown in FIG. 37(a), fixing-holding forceps 160 have a pair of jaws 162a and 162b at a distal end 161 for holding tissue. The jaws 162a and 162bhave side holes 163a and 163b, and their distal end openings 164a and 164b are positioned near the distal ends of the jaws 162a and 162b. The side holes 163a and 163b are large enough to pass a suture and are preferably at least 1 mm.

The fixing-holding forceps 160 can have a composition as shown in FIG. 37(b). FIG. 37(b) is a view of the distal end with the jaws 162a and 162b of the fixing-holding forceps 160 opened. The jaws 162a and 162b have side holes 165a and 165b near the distal end. Slits 166a and 166b are extended from the side holes 165a and 165b to the sides of the jaws 162a and 162b. The side holes 165a and 165b and the slits 166a and 166b are large enough to pass the suture, or preferably at least 1 mm.

As shown in FIGS. 38(a) and (b), the suture 54 is inserted in the jaws 162a and 162b and the side holes 163a and 163b or 165a and 165b. In the case shown in FIG. 37(b), the suture 54 is inserted through the slits 166a and 166b to the side holes 165a and 165b.

Then, while the suture ends 55a and 55b are held and pulled, the second endoscope 57 is advanced again into the body lumen.

As the second endoscope 57 is advanced, the knot 69 is also pushed forward by the distal ends of the jaws 162a and 162b while it is observed under the second endoscope 57.

When the knot 69 reaches the esophageal wall 67, the jaws 162a and 162b open, and the suture ends 55a and 55b are pulled to fix the knot 69.

Opening the jaws 162a and 162b applies more tensile strength to the suture 54 proximal to the knot 69, thus fixing the knot 69 firmly. This means that a formed valve is maintained reliably for a long time.

The fixing-holding forceps 160 hold a knot of the suture and do not require another knot pusher. Therefore, medical costs and preparation time are reduced.

The outer diameter of the second endoscope 57 to which only one outer channel 51 is mounted is smaller than that of the first endoscope 27 to which two outer sheaths 7a and 7b of the piercing device are mounted. The fixing-holding forceps 160 attached to the second endoscope have a means for delivering a knot of the suture to make it easy to insert an endoscope into the body.

The above compositions achieve the following performance.

The fixing means inserted in the second endoscope, which is different from the first endoscope attached the piercing device, can pull down body tissue while it is held and fixed reliably. The fixing means is brought into contact with the body tissue under observation by the endoscope for easy operation and reduced time.

The first endoscope and the piercing device are provided separately from the second endoscope and the fixing means. Therefore, an operator can control the pull of the cardia or the position of the needle entering point and form a valve of any shape according to the condition of a particular patient.

The piercing device integrates two penetration needles. When the distal end of the first endoscope attached the piercing device approaches a penetration point on the esophageal wall, two needles are ready to be penetrated. Treatment is simplified with reduced operation time.

The piercing device makes the inner sheath touch the penetration point before penetration. It makes it easy to locate the penetration point and reliably penetrates toward the inside of the stomach through the esophagogastric junction. If a large valve is not required, it is formed without holding or fixing body tissue using the fixing means. It further simplifies treatment and reduces operation time remarkably.

The piercing device has two penetration needles which are parallel and a certain distance apart from each other. Therefore, the two entering points or two exiting points should also be a certain distance apart. As a result, an area of body tissue to be contracted by a suture cannot be too small. It is extended over a certain area and formed into a valve of desired size.

Two penetration needles are mounted at specified points on the cap at the distal end of the piercing device. Only by connecting the cap to the distal end of the first endoscope can the two penetration needles be mounted at the specified points against the distal end of the first endoscope. It reduces time for mounting them on the endoscope.

The piercing device or the fixing means is equipped with a means for pushing a knot of the suture. It eliminates preparing another knot pusher. Medical costs and preparation time are reduced.

Also the piercing device is inserted into a body lumen without damaging it because the needles can be housed in the piercing device.

What is claimed is:

1. A treatment system, to be used with an endoscope for suturing or ligating tissues in body cavities, said treatment system comprising:
    first and second endoscopes for peroral insertion through body cavities;
    a tissue piercing device mountable to the first endoscope, said tissue piercing device having two piercing members each comprising a needle, said two needles being parallel and spaced apart at a constant interval;
    a tissue fixing device projecting from a distal end of the second endoscope for fixing a site to be pierced;
    one suture holding device slidably inserted through the second endoscope; and
    two sutures respectively slidably inserted through the two needles of the tissue piercing device;
    wherein said one suture holding device comprises a loop at a distal end thereof, and wherein a longest length of an opening of the loop is longer than the interval between the two needles so that the loop is adapted to capture the two sutures extending from the two needles and to simultaneously pull the two sutures.

2. A treatment system according to claim 1,
    wherein a driving member for rotating, advancing, and retracting the loop is connected to a proximal end of the loop; and
    wherein a center axis of the loop is inclined with respect to a longitudinal axis of the driving member.

* * * * *